United States Patent
Park et al.

(10) Patent No.: US 10,487,128 B2
(45) Date of Patent: Nov. 26, 2019

(54) CONJUGATE OF BIOLOGICALLY ACTIVE POLYPEPTIDE MONOMER AND IMMUNOGLOBULIN FC FRAGMENT WITH REDUCED RECEPTOR-MEDIATED CLEARANCE, AND THE METHOD FOR PREPARING THE SAME

(71) Applicant: HANMI PHARM. CO., LTD., Hwaseong-si, Gyeonggi-do (KR)

(72) Inventors: Sung Hee Park, Seongnam-si (KR); Min Young Kim, Anseong-si (KR); Hyung Kyu Lim, Hwaseong-si (KR); Sung Min Bae, Seongnam-si (KR); Sung Youb Jung, Suwon-si (KR); Se Chang Kwon, Seoul (KR)

(73) Assignee: HANMI PHARM. CO., LTD, Hwaseong-Si (KR)

(*) Notice: Subject to any disclaimer, the term of this patent is extended or adjusted under 35 U.S.C. 154(b) by 10 days.

(21) Appl. No.: 14/904,254

(22) PCT Filed: Jul. 14, 2014

(86) PCT No.: PCT/KR2014/006329
§ 371 (c)(1),
(2) Date: Jan. 11, 2016

(87) PCT Pub. No.: WO2015/005748
PCT Pub. Date: Jan. 15, 2015

(65) Prior Publication Data
US 2016/0158378 A1    Jun. 9, 2016

(30) Foreign Application Priority Data
Jul. 12, 2013 (KR) .................. 10-2013-0082511

(51) Int. Cl.
*C07K 14/605* (2006.01)
*C07K 16/00* (2006.01)
*C07K 14/435* (2006.01)
*A61K 47/68* (2017.01)
*A61K 38/00* (2006.01)

(52) U.S. Cl.
CPC .......... *C07K 14/605* (2013.01); *A61K 47/68* (2017.08); *A61K 47/6811* (2017.08); *C07K 14/435* (2013.01); *C07K 16/00* (2013.01); *A61K 38/00* (2013.01); *C07K 2317/41* (2013.01); *C07K 2317/53* (2013.01); *C07K 2319/30* (2013.01)

(58) Field of Classification Search
CPC .... C07K 14/605; C07K 16/00; C07K 14/435; C07K 2319/30; A61K 47/68; A61K 47/6811; A61K 38/00
See application file for complete search history.

(56) References Cited

U.S. PATENT DOCUMENTS

| | | |
|---|---|---|
| 5,116,964 A | 5/1992 | Capon et al. |
| 5,349,053 A | 9/1994 | Landolfi |
| 5,605,690 A | 2/1997 | Jacobs et al. |
| 5,712,121 A | 1/1998 | Devos et al. |
| 5,723,125 A | 3/1998 | Chang et al. |
| 6,277,375 B1 | 8/2001 | Ward |
| 6,410,008 B1 | 6/2002 | Strom et al. |
| 6,444,792 B1 | 9/2002 | Gray et al. |
| 6,451,313 B1 | 9/2002 | Maddon et al. |
| 8,431,132 B2 | 4/2013 | Wang et al. |
| 2005/0202538 A1 | 9/2005 | Gillies et al. |
| 2009/0053246 A1 | 2/2009 | Kim et al. |
| 2012/0244578 A1 | 9/2012 | Kannan et al. |

FOREIGN PATENT DOCUMENTS

| | | |
|---|---|---|
| CN | 1723219 A | 1/2006 |
| CN | 102869371 A | 1/2013 |
| JP | 2008-169195 A | 7/2008 |
| JP | 2012-520873 A | 9/2012 |
| KR | 10-0249572 B1 | 3/2000 |
| KR | 10-2003-0009464 A | 1/2003 |
| KR | 10-2005-0047032 A | 5/2005 |

(Continued)

OTHER PUBLICATIONS

Eizo Sada, et al., "Resistance to Proteolysis of Antibody Ligands Modified with Polyethylene Glycol", Journal of Fermentation and Bioengineering, 1991, pp. 137-139, vol. 71, No. 2.

(Continued)

*Primary Examiner* — Ruixiang Li
(74) *Attorney, Agent, or Firm* — Sughrue Mion, PLLC

(57) ABSTRACT

Provided is a long-acting pharmaceutical composition containing a conjugate comprising a physiologically active polypeptide linked to an immunoglobulin Fc fragment, wherein the composition contains a monomeric conjugate comprising one molecule of the physiologically active polypeptide linked to a single immunoglobulin Fc fragment, and optionally contains a multimeric conjugate comprising two or more molecules of the same physiologically active polypeptide linked to a single immunoglobulin Fc fragment, provided that the molar ratio of the monomeric conjugate to the multimeric conjugate in the composition is at least 19; a physiologically active polypeptide monomer-immunoglobulin Fc fragment conjugate that comprises a physiologically active polypeptide monomer linked via a non-peptidyl linker to an immunoglobulin Fc fragment, wherein the physiologically active polypeptide is linked via the non-peptidyl linker to the immunoglobulin Fc fragment in a monomeric form.

13 Claims, 3 Drawing Sheets

Specification includes a Sequence Listing.

(56) References Cited

FOREIGN PATENT DOCUMENTS

| | | |
|---|---|---|
| KR | 10-2006-0106486 A | 10/2006 |
| KR | 10-0725315 B1 | 6/2007 |
| KR | 10-2009-0008151 A | 1/2009 |
| KR | 10-2012-0137271 A | 12/2012 |
| WO | 96/32478 A1 | 10/1996 |
| WO | 97/34631 A1 | 9/1997 |
| WO | 00/23472 A2 | 4/2000 |
| WO | 01/03737 A1 | 1/2001 |
| WO | 2005/047334 A1 | 5/2005 |
| WO | 2005/047336 A1 | 5/2005 |
| WO | 2005/047337 A1 | 5/2005 |
| WO | 2006/107124 A1 | 10/2006 |
| WO | 2010/011096 A2 | 1/2010 |
| WO | 2011/122921 A2 | 10/2011 |
| WO | 2012/173422 A1 | 12/2012 |
| WO | 2013/066106 A1 | 5/2013 |

OTHER PUBLICATIONS

International Searching Authority, International Search Report of PCT/KR2014/006329, dated Nov. 4, 2014. [PCT/ISA/210].

International Searching Authority, Written Opinion of PCT/KR2014/006329, dated Nov. 4, 2014. [PCT/ISA/237].

Picha, Kristen M. et al., "Protein Engineering Strategies for Sustained Glucagon-Like Peptide-1 Receptor-Dependent Control of Glucose Homeostasis", Diabetes, Jul. 1, 2008, XP-002547063, vol. 57, No. 7, pp. 1926-1934.

Glaesner, Wolfgang et al., "Engineering and characterization of the long-acting glucagon-like peptide-1 analogue LY2189265, an Fc fusion protein", Diabetes/Metabolism Research and Reviews, Apr. 30, 2010, vol. 26, No. 4, XP055181624, pp. 287-296.

European Patent Office; Communication dated Dec. 9, 2016 in counterpart European application No. 14823791.0.

Hungarian Patent Office; Communication dated Jan. 9, 2017 in counterpart Hungarian application No. P1600209/13.

Hungarian Intellectual Property Office, Communication dated Apr. 20, 2016 issued in corresponding Hungarian Application No. P1600209.

Japanese Patent and Trademark Office; communication dated Mar. 5, 2018, in Japanese Patent Application No. 2016-525295.

Chinese Patent and Trademark Office; communication dated Mar. 8, 2018, in Chinese Patent Application No. 201480048797.0.

"Antibody Fragmentation", ThermoFisher Scientific, Retrieved from the internet https://www.thermofisher.com/jp/ja/home/life-science/protein-biology/protein-biology-learning-center/protein-biology-resource-library/pierce-protein-methods/anitbody-fragmentation.html; pp. 1-8 (15 pages total).

Japanese Patent Office; Communication dated Nov. 29, 2018 in counterpart application No. 2016-525295.

Communication dated Feb. 11, 2019, from the Israel Patent Office in counterpart application No. 243568.

CONJUGATE OF BIOLOGICALLY ACTIVE POLYPEPTIDE MONOMER AND IMMUNOGLOBULIN FC FRAGMENT WITH REDUCED RECEPTOR-MEDIATED CLEARANCE, AND THE METHOD FOR PREPARING THE SAME

CROSS REFERENCE TO RELATED APPLICATIONS

This application is a National Stage of International Application No. PCT/KR2014/006329 filed Jul. 14, 2014, claiming priority based on Korean Patent Application No. 10-2013-0082511, filed Jul. 12, 2013, the contents of all of which are incorporated herein by reference in their entirety.

TECHNICAL FIELD

The present invention relates to: a long-acting pharmaceutical composition containing a conjugate comprising a physiologically active polypeptide linked to an immunoglobulin Fc fragment, wherein the composition contains a monomeric conjugate comprising one molecule of the physiologically active polypeptide linked to a single immunoglobulin Fc fragment, and optionally contains a multimeric conjugate comprising two or more molecules of the same physiologically active polypeptide linked to a single immunoglobulin Fc fragment, provided that the molar ratio of the monomeric conjugate to the multimeric conjugate in the composition is at least 19; a physiologically active polypeptide monomer-immunoglobulin Fc fragment conjugate that comprises a physiologically active polypeptide monomer linked via a non-peptidyl linker to an immunoglobulin Fc fragment, wherein the physiologically active polypeptide is linked via the non-peptidyl linker to the immunoglobulin Fc fragment in a monomeric form, the conjugate showing reduced receptor-mediated internalization or receptor-mediated clearance compared to either a dimeric conjugate comprising two molecules of the physiologically active polypeptide linked via the non-peptidyl linker to a single immunoglobulin Fc fragment, or a conjugate comprising a physiologically active polypeptide dimer linked in-frame to the immunoglobulin Fc fragment; and a method for preparing the long-acting pharmaceutical composition.

BACKGROUND ART

It is known that proteins in vivo are cleared by various mechanisms, including degradation by serum proteases, elimination through the kidneys, or clearance by receptors. Thus, various attempts have been made to avoid such protein clearance mechanisms to increase the half-life of physiologically active proteins to thereby enhance their therapeutic efficacy. Particularly, studies have been conducted on protein conjugates that comprise a polyethylene glycol polymer (PEG), albumin, fatty acid or an antibody Fc fragment (constant region) linked to a protein in order to increase the half-life of the protein. Such studies aim to covalently link this material to a physiologically active protein in order to increase the serum half-life of the physiologically active protein and shorten the interval of drug administration to thereby increase the patient's convenience. Particularly, in order to stabilize proteins and inhibit their contact with proteases and their elimination through the kidneys, a method of chemically attaching highly soluble polymers such as PEG to the surface of the protein drugs is used. In the case of this method, it is known that a polymer binds non-specifically to a specific site or various sites of a target protein to increase the solubility of the protein, stabilize the protein and prevent the hydrolysis of the protein, and furthermore, causes no particular side effects (Sada et al., J. Fermentation Bioengineering 71: 137-139, 1991). However, this method has problems in that even though the PEG linked to the physiologically active protein can increase the stability of the protein, it significantly reduces the titer of the protein, and as the molecular weight of the PEG increases, its reactivity with the protein decreases, resulting in a decrease in the yield. In addition, when a specific amino acid residue of a protein is modified with fatty acids, the modified fatty acid binds reversibly to serum albumin to increase the serum half-life of the protein, but the half-life is about one day to one week, indicating that the increasing the half-life is not so significant. In addition, there is a disadvantage in that the physiologically active protein reversibly dissociated from albumin is easily eliminated through the kidneys.

For these reasons, efforts have been made to use immunoglobulin fragments to increase the half-life of physiologically active materials, including proteins. Particularly, studies have been actively conducted to increase the stability of therapeutic proteins by fusing the therapeutic proteins with such immunoglobulin Fc fragments.

It is known to express interferon (Korean Patent Laid-Open Publication No. 2003-9464), interleukin-4 receptor, interleukin-7 receptor or erythropoietin receptor (Korean Patent No. 249572) as a fusion with an immunoglobulin Fc fragment in a mammal by a genetic recombination method. Also, International Patent Publication No. WO 01/03737 discloses a fusion protein comprising a cytokine or growth factor linked to an immunoglobulin Fc fragment via an oligopeptide linker. Moreover, U.S. Pat. No. 5,116,964 discloses a fusion protein comprising an LHR (lymphocyte cell surface glycoprotein) or CD4 protein fused to the amino or carboxy terminal end of an immunoglobulin Fc fragment by a genetic recombination method, and U.S. Pat. No. 5,349,053 discloses a fusion protein of IL-2 with an immunoglobulin Fc fragment. In addition, examples of Fc fusion proteins prepared by genetic recombination methods include a fusion protein of interferon-beta or its derivative with an immunoglobulin Fc fragment (International Patent Publication No. WO 00/23472), a fusion protein of IL-5 receptor with an immunoglobulin Fc fragment (U.S. Pat. No. 5,712,121), a fusion protein of interferon-alpha with an immunoglobulin G4 Fc fragment (U.S. Pat. No. 5,723,125), and a fusion protein of CD4 protein with an immunoglobulin G2 Fc fragment (U.S. Pat. No. 6,451,313). Additionally, U.S. Pat. No. 5,605,690 relates to the modification of amino acid residues in an immunoglobulin Fc fragment and discloses a TNFR-IgG1 Fc fusion protein prepared by a genetic recombination method using an Fc fragment obtained by modifying the amino acid residues of a particular complement-binding site or a receptor-binding site in an immunoglobulin Fc fragment. Furthermore, methods of preparing fusion proteins by a genetic recombination method using the immunoglobulin Fc region modified as described above are also disclosed in U.S. Pat. Nos. 6,277,375, 6,410,008 and 6,444,792. However, bio-medicines having an immunoglobulin Fc fragment fused thereto are required to overcome cytotoxic problems caused by the effector function inherent of the Fc fragment.

DISCLOSURE

Technical Problem

The present inventors have made extensive efforts to prepare a conjugate having an increased serum in vivo half-life by an immunoglobulin Fc fragment to a physiologically active polypeptide. As a result, the present inventors have found that, when a physiologically active polypeptide is linked to an immunoglobulin Fc fragment in a monomeric form, it shows significantly reduced receptor-mediated clearance and also shows a long half-life even in a rat animal model, compared to when the physiologically active polypeptide is present in a multimeric form, thereby completing the present invention.

Technical Solution

It is an object of the present invention to provide a long-acting pharmaceutical composition containing a conjugate comprising a physiologically active polypeptide linked to an immunoglobulin Fc fragment, wherein the composition contains a monomeric conjugate comprising one molecule of the physiologically active polypeptide linked to a single immunoglobulin Fc fragment, and optionally contains a multimeric conjugate comprising two or more molecules of the same physiologically active polypeptide linked to a single immunoglobulin Fc fragment, provided that the molar ratio of the monomeric conjugate to the multimeric conjugate in the composition is at least 19.

Another object of the present invention is to provide a physiologically active polypeptide monomer-immunoglobulin Fc fragment conjugate that comprises a physiologically active polypeptide monomer linked via a non-peptidyl linker to an immunoglobulin Fc fragment, wherein the physiologically active polypeptide is linked via the non-peptidyl linker to the immunoglobulin Fc fragment in a monomeric form, the conjugate showing reduced receptor-mediated internalization or receptor-mediated clearance compared to a conjugate comprising a physiologically active polypeptide linked in-frame to the immunoglobulin Fc fragment.

Still another object of the present invention is to provide a method for preparing the long-acting pharmaceutical composition, the method comprising: (a) linking a physiologically active polypeptide to an immunoglobulin Fc fragment to prepare a mixture of physiologically active polypeptide-immunoglobulin Fc fragment conjugates; and (b) separating from the mixture a physiologically active polypeptide monomer-immunoglobulin Fc fragment conjugate comprising one molecule of the physiologically active polypeptide linked to a single immunoglobulin Fc fragment.

Advantageous Effects

As described above, the inventive conjugate comprising the physiologically active polypeptide monomer linked to the immunoglobulin Fc conjugate shows significantly reduced receptor-mediated internalization or receptor-mediated clearance, and thus has an increased serum half-life. Accordingly, the conjugate of the present invention can provide a drug having an increased serum half-life and therapeutic superiority.

BEST MODE

Figure 1:
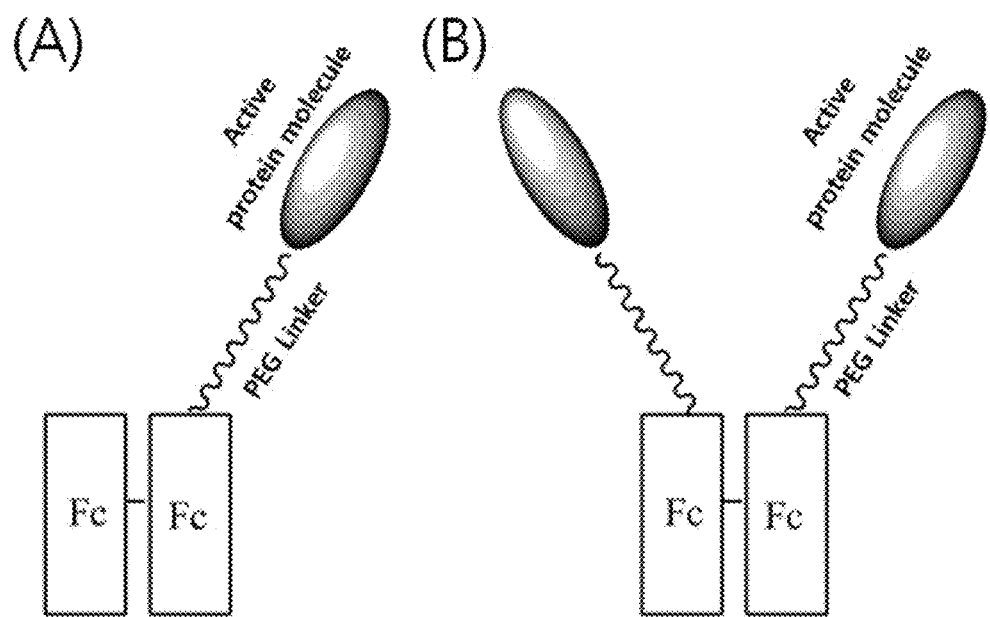
FIG. 1 schematically shows the representative structure of a physiologically active polypeptide monomer-Fc conjugate (FIG. 1A) and the most major configuration of a physiologically active polypeptide dimer-Fc conjugate (FIG. 1B).

To achieve the above objects, in one aspect, the present invention provides a long-acting pharmaceutical composition containing a conjugate comprising a physiologically active polypeptide linked to an immunoglobulin Fc fragment, wherein the composition contains a monomeric conjugate comprising one molecule of the physiologically active polypeptide linked to a single immunoglobulin Fc fragment, and optionally contains a multimeric conjugate comprising two or more molecules of the same physiologically active polypeptide linked to a single immunoglobulin Fc fragment, provided that the molar ratio of the monomeric conjugate to the multimeric conjugate in the composition is at least 19.

In one embodiment, the conjugate that is included in the long-acting pharmaceutical composition may comprise a non-peptidyl linker interposed between the physiologically active polypeptide and the immunoglobulin Fc fragment to link the physiologically active polypeptide to the immunoglobulin Fc fragment.

In another embodiment, the monomeric conjugate may show reduced receptor-mediated internalization or receptor-mediated clearance compared to either a dimeric conjugate comprising two molecules of the physiologically active polypeptide linked via the non-peptidyl linker to a single immunoglobulin Fc fragment, or a conjugate comprising a physiologically active polypeptide dimer linked in-frame to the immunoglobulin Fc fragment.

In still another embodiment, the physiologically active polypeptide may be selected from the group consisting of glucagon-like peptide-1 (GLP-1), granulocyte colony stimulating factor (G-CSF), human growth hormone (hGH), erythropoietin (EPO), glucagon, oxyntomodulin, insulin, growth hormone releasing hormone, growth hormone releasing peptide, interferons, interferon receptors, G-protein-coupled receptor, interleukins, interleukin receptors, enzymes, interleukin binding proteins, cytokine binding proteins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX and XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, cell surface antigens, virus derived vaccine antigens, monoclonal antibodies, polyclonal antibodies, and antibody fragments.

In still another embodiment, the physiologically active polypeptide may be selected from the group consisting of glucagon-like peptide-1 (GLP-1), granulocyte colony stimulating factor (G-CSF), human growth hormone (hGH), erythropoietin (EPO), glucagon, oxyntomodulin, insulin, and derivatives thereof.

In still another embodiment, the non-peptidyl linker may be selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and combinations thereof.

In still another embodiment, the non-peptidyl linker may have a molecular weight ranging from 1 to 100 kDa.

In still another embodiment, the immunoglobulin Fc fragment may be composed of 1 to 4 domains selected from the group consisting of CH1, CH2, CH3 and CH4 domains.

In still another embodiment, the immunoglobulin Fc fragment may further comprise a hinge region.

In still another embodiment, the immunoglobulin Fc fragment may be selected from the group consisting of IgG, IgA, IgD, IgE, IgM, combinations thereof and hybrids thereof.

In still another embodiment, the immunoglobulin Fc fragment may be an IgG4 Fc fragment.

In still another embodiment, the immunoglobulin Fc fragment may be in a non-glycosylated form.

In another aspect, the present invention provides a physiologically active polypeptide monomer-immunoglobulin Fc fragment conjugate that comprises a physiologically active polypeptide monomer linked via a non-peptidyl linker to an immunoglobulin Fc fragment, wherein the physiologically active polypeptide is linked via the non-peptidyl linker to the immunoglobulin Fc fragment in a monomeric form, the conjugate showing reduced receptor-mediated internalization or receptor-mediated clearance compared to either a dimeric conjugate comprising two molecules of the physiologically active polypeptide linked via the non-peptidyl linker to a single immunoglobulin Fc fragment, or a conjugate comprising a physiologically active polypeptide dimer linked in-frame to the immunoglobulin Fc fragment.

In still another aspect, the present invention provides a method for preparing the long-acting pharmaceutical composition, the method comprising: (a) linking a physiologically active polypeptide to an immunoglobulin Fc fragment to prepare a mixture of physiologically active polypeptide-immunoglobulin Fc fragment conjugates; and (b) separating from the mixture a physiologically active polypeptide monomer-immunoglobulin Fc fragment conjugate comprising one molecule of the physiologically active polypeptide linked to a single immunoglobulin Fc fragment.

In one embodiment, the physiologically active polypeptide and the immunoglobulin Fc fragment, which are included in the conjugate in the method, may be linked to each other via a non-peptidyl linker.

In still another embodiment, the conjugate comprising one molecule of the physiologically active polypeptide linked to a single immunoglobulin Fc fragment in the method may show reduced receptor-mediated internalization or receptor-mediated clearance compared to either a dimeric conjugate comprising two molecules of the physiologically active polypeptide linked via the non-peptidyl linker to a single immunoglobulin Fc fragment, or a conjugate comprising a physiologically active polypeptide dimer linked in-frame to the immunoglobulin Fc fragment.

MODE FOR INVENTION

In one aspect, the present invention provides a long-acting pharmaceutical composition containing a conjugate comprising a physiologically active polypeptide linked to an immunoglobulin Fc fragment, wherein the composition contains a monomeric conjugate comprising one molecule of the physiologically active polypeptide linked to a single immunoglobulin Fc fragment, and optionally contains a multimeric conjugate comprising two or more molecules of the same physiologically active polypeptide linked to a single immunoglobulin Fc fragment, provided that the molar ratio of the monomeric conjugate to the multimeric conjugate in the composition is at least 19.

In an embodiment of the present invention, it was found that a conjugate comprising a physiologically active polypeptide monomer linked to an immunoglobulin Fc fragment showed reduced receptor-mediated internalization and receptor-mediated clearance compared to a conjugate comprising a physiologically active polypeptide multimer, particularly a physiologically active polypeptide dimer, linked to an immunoglobulin Fc fragment, and thus may have an increased serum half-life. Thus, it was found that a drug comprising a conjugate, which comprises a physiologically active polypeptide monomer linked to an immunoglobulin Fc fragment to show reduced receptor-mediated clearance, can be used as a long-acting drug, because it shows reduced receptor-mediated internalization and receptor-mediated clearance. In other words, the present invention is based on the finding that a physiologically active polypeptide monomer-immunoglobulin Fc fragment conjugate shows reduced receptor-mediated internalization and receptor-mediated clearance compared to a multimeric conjugate, particularly a dimeric conjugate.

As used herein, the term "long-acting pharmaceutical composition" refers to a pharmaceutical composition containing a physiologically active polypeptide monomer-immunoglobulin Fc fragment conjugate that shows reduced receptor-mediated internalization and receptor-mediated clearance compared to the physiologically active polypeptide itself or a physiologically active polypeptide multimer-immunoglobulin Fc fragment. In other words, the term refers to a pharmaceutical composition containing a monomeric conjugate that comprises one molecule of a physiologically active polypeptide linked to a single immunoglobulin Fc fragment. In addition, the term "pharmaceutical composition" may be used interchangeably with the term "formulation".

In the pharmaceutical composition of the present invention, a monomeric conjugate comprising one molecule of a physiologically active polypeptide linked to a single immunoglobulin Fc fragment may be present at a molar ratio of at least 19:1, preferably at least 99:1, more preferably at least 500:1, relative to a multimeric conjugate comprising two or more molecules of the same physiologically active polypeptide linked to the immunoglobulin Fc fragment. In other words, the long-acting pharmaceutical composition is characterized in that the molar ratio of the monomeric conjugate to the multimeric conjugate ([monomeric conjugate]/[multimeric conjugate]) is at least 19.

According to an embodiment of the present invention, the physiologically active polypeptide in the physiologically active polypeptide-nonpeptidyl polymer-immunoglobulin Fc fragment conjugate is present in a monomeric form, and in this case, the conjugate has a longer in vivo duration of action compared to in the case in which the physiologically active polypeptide is present in a dimeric form. Thus, in the case of a composition in which only a monomeric conjugate is present as a conjugate without a multimeric conjugate or in which the molar ratio of the monomeric conjugate to a multimeric conjugate, particularly a dimeric conjugate, is at least 19, the composition has an excellent effect of increasing the serum half-life of the physiologically active polypeptide, compared to other compositions.

Particularly, the monomeric conjugate according to the present invention has a long in vivo duration of action, because internalization mediated by a receptor of the physiologically active polypeptide is reduced compared to a multimeric conjugate comprising two or more molecules of the physiologically active polypeptide linked to the immunoglobulin Fc fragment. In particular, it is known that renal elimination, another mechanism that determines the half-life of a molecule, depends on the molecular weight of the molecule. Thus, if renal elimination was an important variable that determines the half-life, the half-life would increase as the ratio of a multimeric conjugate having a higher molecular weight would increase. However, in the present invention, it was found that a monomeric conjugate showed a longer in vivo duration of action. In this regard, it can be seen that receptor-mediated internalization is an important factor in increasing the in vivo half-life of the conjugate according to the present invention. Such results can be attributable to the advantageous effects (e.g., reduced steric hindrance) of the monomeric conjugate, which cannot be found in the multimeric conjugate.

Thus, the long-acting pharmaceutical composition of the present invention can show a longer in vivo duration of action compared to a pharmaceutical composition comprising either a physiologically active polypeptide multimer-immunoglobulin Fc fragment conjugate or a conjugate comprising a physiologically active polypeptide dimer linked in-frame to the immunoglobulin Fc. Particularly, in the pharmaceutical composition of the present invention, a monomeric conjugate comprising one molecule of a physiologically active polypeptide linked to a single immunoglobulin Fc fragment may be present at a molar ratio of at least 19:1, preferably at least 99:1, more preferably at least 500:1, relative to a multimeric conjugate comprising two or more molecules of the same physiologically active polypeptide linked to the immunoglobulin Fc fragment, and in this case, the composition comprising the monomeric conjugate and the multimeric conjugate provides an excellent long-lasting formulation, because the in vivo half-life of the composition is not reduced.

As used herein, the term "physiologically active polypeptide-immunoglobulin Fc fragment conjugate" refers to a conjugate comprising a physiologically active polypeptide conjugated to an immunoglobulin Fc fragment. Preferably, the conjugate may comprise a non-peptidyl linker interposed between the physiologically active polypeptide and the immunoglobulin Fc fragment to link the physiologically active polypeptide to the immunoglobulin Fc fragment.

As used herein, the term "physiologically active polypeptide monomer-immunoglobulin Fc fragment conjugate" refers to a conjugate comprising a physiologically active polypeptide monomer conjugated to an immunoglobulin Fc fragment. The conjugate includes a form in which a single physiologically active polypeptide is linked to a single immunoglobulin Fc fragment. Herein, the single immunoglobulin Fc fragment preferably is in a form in which two Fc chains are linked to each other by, for example, a disulfide bond, but is not limited thereto. The structure of this physiologically active polypeptide monomer-immunoglobulin Fc fragment conjugate is illustrated in FIG. 1, but is not limited thereto. In the specification, the term "physiologically active polypeptide monomer-immunoglobulin Fc fragment conjugate" is used interchangeably with the term "monomeric conjugate".

The physiologically active polypeptide monomer-immunoglobulin Fc fragment conjugate is characterized in that it shows reduced receptor-mediated internalization or receptor-mediated clearance compared to either a multimeric conjugate comprising two or more molecules of the physiologically active polypeptide linked to a single immunoglobulin Fc fragment, or a conjugate comprising a physiologically active polypeptide multimer linked in-frame to the immunoglobulin Fc fragment. Thus, a drug, which comprises the physiologically active polypeptide monomer-immunoglobulin Fc fragment conjugate alone or comprises the conjugate at a high ratio, shows a long in vivo duration of action and excellent therapeutic efficacy.

Meanwhile, the multimeric conjugate comprising two or more molecules of the physiologically active polypeptide linked to the immunoglobulin Fc fragment includes a form in which two or more molecules of the physiologically active polypeptide is linked to a single immunoglobulin Fc fragment (e.g., composed of two Fc chains linked to each other by a disulfide bond or the like).

Particularly, the physiologically active polypeptide dimer-immunoglobulin Fc fragment conjugate includes a form in which two molecules of the physiologically active polypeptide linked to a single immunoglobulin Fc fragment (e.g., composed of two Fc chains linked to each other by a disulfide bond or the like). Herein, the physiologically active polypeptide may be linked via a non-peptidyl linker to each of two chains constituting the immunoglobulin Fc fragment, but is not limited thereto. This configuration is shown in FIG. 1(B).

In addition, the in-frame conjugate includes a form in which a physiologically active polypeptide multimer, particularly a physiologically active polypeptide dimer, is linked in-frame to a single immunoglobulin Fc fragment, and also a multimer, wherein two or more fusion polypeptides comprising a physiologically active polypeptide is fused with an immunoglobulin Fc fragment are formed.

Meanwhile, in the physiologically active polypeptide monomer-immunoglobulin Fc fragment according to the present invention, the physiologically active polypeptide monomer is covalently linked via a non-peptidyl linker to the immunoglobulin Fc fragment.

As used herein, the term "non-peptidyl linker" refers to a biocompatible polymer composed of two or more repeating units linked to each other, in which the repeating units are linked to each other by any non-peptide covalent bond. This non-peptidyl linker may have two ends or three ends.

The non-peptidyl linker that is used in the present invention may be selected from the group consisting of polyethylene glycol, polypropylene glycol, a copolymer of ethylene glycol with propylene glycol, polyoxyethylated polyol, polyvinyl alcohol, polysaccharide, dextran, polyvinyl ethyl ether, biodegradable polymers such as polylactic acid (PLA) and polylactic-glycolic acid (PLGA), lipid polymers, chitins, hyaluronic acid, and combinations thereof, but is not limited thereto. Preferably, it is polyethylene glycol.

In addition, their derivatives known in the art and derivatives that can be easily prepared in the state of the art also fall within the scope of the present invention.

A peptidyl linker that is used in a fusion protein prepared by a conventional in-frame fusion method has a disadvantage in that it is easily cleaved by protease in vivo, and thus the expected effect of increasing the serum half-life of the active drug by a carrier cannot also be obtained. For this reason, in addition to the peptidyl linker, a non-peptidyl linker may be used in the present invention to prepare the conjugate. The non-peptidyl linker may be a polymer that has resistance to protease to maintain the serum half-life of the peptide, similar to that of a carrier. Therefore, any non-peptidyl linker may be used in the present invention without any limitation, as long as it is made of a polymer having the above-described function, that is, a polymer having resistance to protease in vivo. The non-peptidyl linker has a molecular weight of 1-100 kDa, preferably 1-20 kDa, but is not limited thereto.

In addition, the non-peptidyl linker that is linked to the immunoglobulin Fc fragment in the present invention may be made not only of one kind of polymer, but also of a combination of different kinds of polymers.

The non-peptidyl linker that is used in the present invention has reactive groups capable of binding to the immunoglobulin Fc fragment and the protein drug.

The reactive groups at both ends of the non-peptidyl polymer are preferably selected from the group consisting of a reactive aldehyde group, a propionaldehyde group, a butyraldehyde group, a maleimide group and a succinimide derivative. Herein, the succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, a physiologically active polypeptide and an immunoglobulin effectively bind to both ends of the non-peptidyl linker, respectively, while minimizing non-specific reactions. A final product generated by reductive alkylation via an aldehyde bond is much more stable than that linked via an amide bond. The aldehyde reactive group can bind selectively to the N-terminus at a low pH and can form a covalent bond with a lysine residue at a high pH, for example, a pH of 9.0.

The reactive groups at both ends of the non-peptidyl linker may be the same or different. For example, one end of the non-peptidyl linker may have a maleimide group, and the other end may have an aldehyde group, a propionaldehyde group, or a butyl aldehyde. When a polyethylene glycol having hydroxyl reactive groups at both ends is used as the non-peptidyl linker, the hydroxy groups may be activated into various reactive groups by a known chemical reaction. Alternatively, a commercially available polyethylene glycol having a modified reactive group may be used to prepare the conjugate of the present invention.

As used herein, the term "physiologically active polypeptide" collectively refers to polypeptides having any physiological activity in vivo, which commonly have a polypeptide structure and have various physiological activities. The physiologically active polypeptides include those that function to regulate genetic expression and physiological function and to correct an abnormal condition caused by the lack or excessive secretion of a substance that is involved in the regulation of functions in vivo. The physiologically active polypeptides may include general protein therapeutic agents.

In the conjugate of the present invention, the kind and size of physiologically active polypeptide are not specifically limited, as long as it can be linked to the immunoglobulin Fc fragment to show reduced receptor-mediated internalization or receptor-mediated clearance compared to when it is linked to the immunoglobulin Fc fragment in a multimeric form. Further, it is more preferably a physiologically active polypeptide, the receptor-mediated internalization and receptor-mediated clearance of which are major in vivo protein clearance mechanisms.

The physiologically active polypeptide may be selected from the group consisting of glucagon-like peptide-1 (GLP-1), granulocyte colony stimulating factor (G-CSF), human growth hormone (hGH), erythropoietin (EPO), glucagon, oxyntomodulin, insulin, growth hormone releasing hormone, growth hormone releasing peptide, interferons, interferon receptors, G-protein-coupled receptor, interleukins, interleukin receptors, enzymes, interleukin binding proteins, cytokine binding proteins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, α-lactalbumin, apolipoprotein-E, highly glycosylated erythropoietin, angiopoietins, hemoglobin, thrombin, thrombin receptor activating peptide, thrombomodulin, blood factors VII, VIIa, VIII, IX and XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, cholecystokinin, pancreatic polypeptide, gastrin releasing peptide, corticotropin releasing factor, thyroid stimulating hormone, autotaxin, lactoferrin, myostatin, cell surface antigens, virus derived vaccine antigens, monoclonal antibodies, polyclonal antibodies, and antibody fragments. Preferably, the physiologically active polypeptide may be selected from the group consisting of glucagon-like peptide-1 (GLP-1), granulocyte colony stimulating factor (G-CSF), human growth hormone (hGH), erythropoietin (EPO), glucagon, oxyntomodulin, insulin, and derivatives thereof, but is not limited thereto.

In addition, the term "physiologically active polypeptide", as used herein, is meant to include not only natural physiologically active polypeptides, but also agonists, precursors, derivatives, fragments or variants of each polypeptide.

The physiologically active polypeptide that is used in the present invention may be a GLP-1 agonist, and an example thereof may be (1H-imidazol-4-yl)-acetyl-1 (GEGTFTSDL SKQMEEEAVR LFIEWLKNGGPSSGAPPPS (SEQ ID NO: 1) (Bachem) or HGEGTFTSDV SSYLEEQAAK EFIAWLVKG (SEQ ID NO: 2) (Bachem)), but is not specifically limited thereto. The amino acid sequence is in the direction from the N-terminus to the C-terminus.

(1H-Imidazol-4-yl)-acetyl-1 (GEGTFTSDL SKQMEEEAVR LFIEWLKNGGPSSGAPPPS (SEQ ID NO: 1) (Bachem)) was used for the preparation of a GLP-1 agonist-immunoglobulin Fc fragment in the Example of the present invention.

Herein, examples of oxyntomodulin derivatives include all those disclosed in Korean Patent Laid-Open Publication No. 10-2012-0137271, and examples of insulin-releasing peptide derivatives include those disclosed in Korean Patent Laid-Open Publication No. 10-2009-0008151, but are not limited thereto.

Because the immunoglobulin Fc region is a biodegradable polypeptide that is metabolized in vivo, it is safe for use as a drug carrier. Also, because the immunoglobulin Fc region has a molecular weight lower than the entire immunoglobulin molecule, it is beneficial in terms of the preparation, purification and yield of the conjugate. In addition, because the Fab region, which displays high non-homogeneity due to the difference in amino acid sequence between antibodies, is removed, the Fc region has greatly increased substance homogeneity and a low potential to induce serum antigenicity.

The term "immunoglobulin Fc region", as used herein, refers to a protein that contains the heavy-chain constant region 2 (CH2) and the heavy-chain constant region 3 (CH3) of an immunoglobulin, excluding the heavy-chain and light-chain variable regions, the heavy-chain constant region 1 (CH1) and the light-chain constant region 1 (CL1) of the immunoglobulin. The immunoglobulin Fc region may further include a hinge region in the heavy-chain constant region. Also, the immunoglobulin Fc region in the present invention may be an extended Fc region that contains a portion or the whole of the heavy-chain constant region 1 (CH1) and/or the light-chain constant region 1 (CL1), except for the heavy-chain and light-chain variable regions, as long as it has a physiological function substantially equal to or better than the native form. Further, it may be a fragment having a deletion in a relatively long portion of the amino acid sequence of CH2 and/or CH3.

In other words, the immunoglobulin Fc region in the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

In the present invention, the immunoglobulin Fc fragment is meant to include not only a native amino acid sequence, but also a sequence mutant thereof. As used herein, the term "amino acid sequence mutant" refers to a sequence that is different from the native amino acid sequence due to a deletion, insertion, non-conservative or conservative substitution or combinations thereof of one or more amino acid residues. For example, in the case of IgG Fc, amino acid residues at positions 214 to 238, 297 to 299, 318 to 322 or 327 to 331, known to be important in binding, may be used as a suitable target for modification.

In addition, various mutants are also possible, including mutants having a deletion of a region capable of forming a disulfide bond, a deletion of several amino acid residues at the N-terminus of a native Fc, or an addition of methionine residue to the N-terminus of a native Fc. Furthermore, to eliminate effector functions, a complement-binding site, for example, a C1q-binding site, may be removed, and an antibody dependent cell mediated cytotoxicity (ADCC) site may also be removed. Techniques of preparing such sequence derivatives of the immunoglobulin Fc fragment are disclosed in International Patent Publication Nos. WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions.

In some case, the immunoglobulin Fc fragment may also be modified by, for example, phosphorylation, sulfation, acrylation, glycosylation, methylation, farnesylation, acetylation or amidation.

The above-described Fc mutants are mutants that show the same biological activity as that of the Fc region of the present invention, but have improved structural stability against heat, pH, or the like.

In addition, these Fc fragments may be obtained from native forms isolated from humans and animals including cows, goats, pigs, mice, rabbits, hamsters, rats and guinea pigs, or may be recombinant forms or derivatives thereof, obtained from transformed animal cells or microorganisms. Herein, they may be obtained from a native immunoglobulin by isolating a whole immunoglobulin from the living body of humans or animals and treating it with protease. When the whole immunoglobulin is treated with papain, it is cleaved into Fab and Fc, and when it is treated with pepsin, it is cleaved into pF'c and F(ab)$_2$. These fragments may be subjected, for example, to size-exclusion chromatography to isolate Fc or pF'c.

Preferably, it is a recombinant immunoglobulin Fc region obtained from a microorganism using a human Fc region.

In addition, the immunoglobulin Fc region may be in the form of having native sugar chains, increased sugar chains compared to a native form or decreased sugar chains compared to the native form, or may be in a deglycosylated form. The increase, decrease or removal of the immunoglobulin Fc sugar chains may be performed using conventional methods, such as a chemical method, an enzymatic method and a genetic engineering method using a microorganism. The immunoglobulin Fc region obtained by removing sugar chains from an Fc shows a sharp decrease in binding affinity for the complement (c1q) and a decrease or loss in antibody-dependent cell-mediated cytotoxicity or complement-dependent cytotoxicity, and thus does not induce unnecessary immune responses in vivo. In this regard, an immunoglobulin Fc fragment in a deglycosylated or aglycosylated form may be more suitable for use as a drug carrier.

As used herein, the term "deglycosylation" means enzymatically removing sugar moieties from an Fc region, and the term "aglycosylation" means an unglycosylated Fc fragment that is produced in a prokaryote, preferably E. coli.

Meanwhile, the immunoglobulin Fc region may originate from humans or animals such as cattle, goats, pigs, mice, rabbits, hamsters, rats or guinea pigs. Preferably, it is of human origin. In addition, the immunoglobulin Fc fragment may be an Fc fragment that is derived from IgG, IgA, IgD, IgE and IgM, combinations thereof, or hybrids thereof. Preferably, it is derived from IgG or IgM, which is among the most abundant proteins in the human blood, and most preferably it is derived from IgG known to enhance the half-life of ligand-binding proteins.

The term "combination", as used herein, means that polypeptides encoding single-chain immunoglobulin Fc fragments of the same origin are linked to a single-chain polypeptide of a different origin to form a dimer or multimer. In other words, a dimer or multimer may be formed from two or more fragments selected from the group consisting of IgG Fc, IgA Fc, IgM Fc, IgD Fc, and IgE Fc fragments.

As used herein, the term "hybrid" means that sequences encoding two or more immunoglobulin Fc fragments of different origins are present in a single-chain immunoglobulin Fc fragment. In the present invention, various types of hybrids are possible. In other words, domain hybrids may be composed of one to four domains selected from the group consisting of CH1, CH2, CH3 and CH4 of IgG Fc, IgM Fc, IgA Fc, IgE Fc and IgD Fc, and may include a hinge region.

On the other hand, IgG can be divided into IgG1, IgG2, IgG3 and IgG4 subclasses, and combinations or hybrids thereof may be used in the present invention. Preferred are IgG2 and IgG4 subclasses, and most preferred is the Fc fragment of IgG4 rarely having effector functions such as CDC (complement dependent cytotoxicity). In other words, the most preferable immunoglobulin Fc fragment for use as a drug carrier in the present invention is a human IgG4-derived unglycosylated Fc fragment. The human Fc fragment is more preferable than a non-human Fc fragment, which may act as an antigen in the human body and cause undesirable immune responses such as the production of a new antibody against the antigen.

Figure 2:
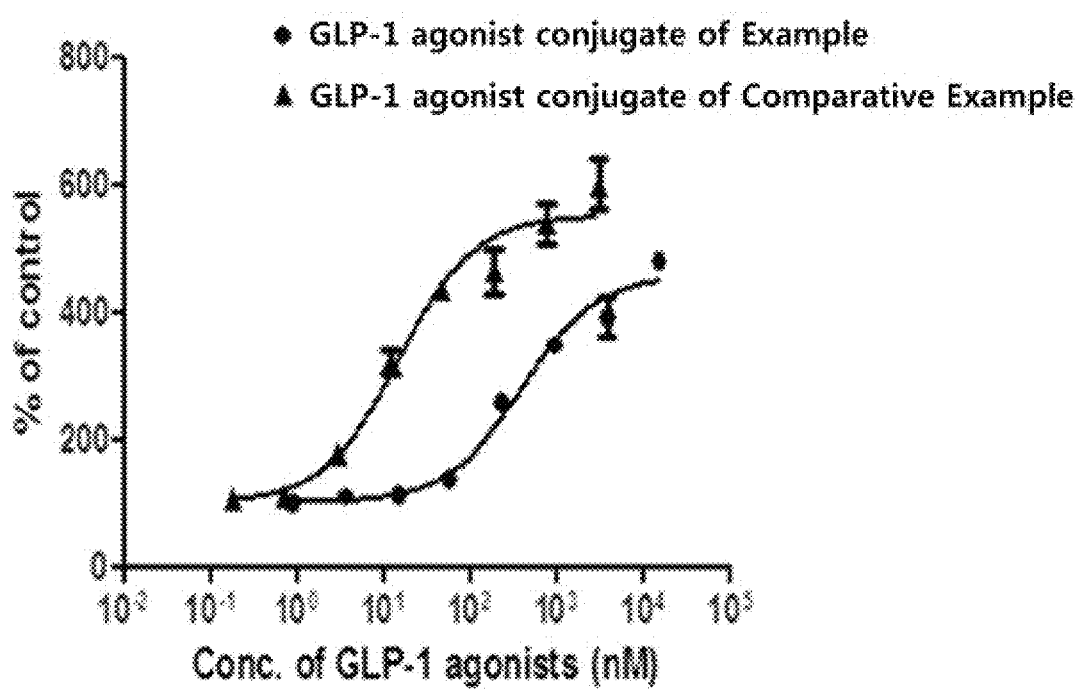
FIG. 2 shows a comparison of the degree of receptor internalization between a GLP-1 agonist-immunoglobulin Fc fragment conjugate (Example of the present invention) and a GLP-1 agonist-immunoglobulin Fc fragment fusion protein in which the GLP-1 agonist is present in a dimeric form (Comparative Example).
Figure 3:
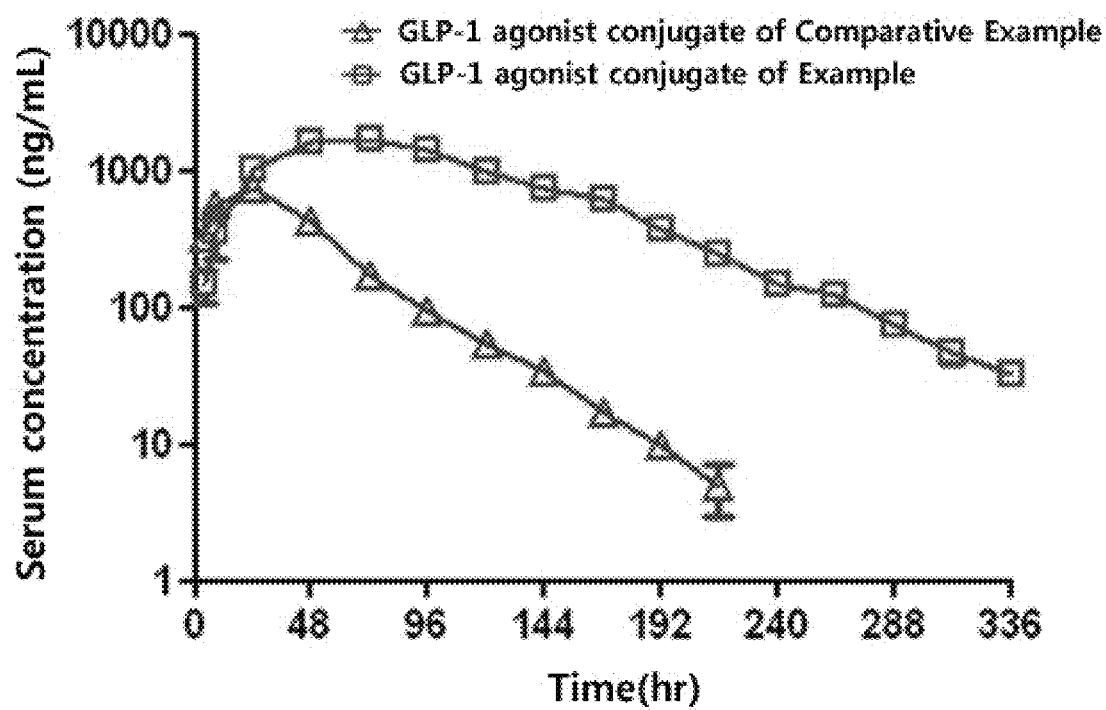
FIG. 3 shows a comparison of in vivo pharmacokinetics between the GLP-1 agonist conjugate of the Example of the present invention and the GLP-1 agonist conjugate of the Comparative Example.

In one example of the present invention, a conjugate was prepared by linking a physiologically active polypeptide monomer via a non-peptidyl polymer to an immunoglobulin Fc fragment (Example), and it was found that the prepared conjugate shows reduced receptor-mediated internalization, and thus has an increased in vivo half-life, compared to a conjugate in the physiologically active polypeptide is present in a dimeric form (FIGS. 2 and 3).

In still another aspect, the present invention provides a physiologically active polypeptide monomer-immunoglobulin Fc fragment conjugate that comprises a physiologically active polypeptide monomer linked via a non-peptidyl linker to an immunoglobulin Fc fragment, wherein the physiologically active polypeptide is linked via the non-peptidyl linker to the immunoglobulin Fc fragment in a monomeric form, the conjugate showing reduced receptor-mediated internalization or receptor-mediated clearance compared to either a dimeric conjugate comprising two molecules of the physiologically active polypeptide linked via the non-peptidyl linker to a single immunoglobulin Fc fragment, or a conjugate comprising a physiologically active polypeptide dimer linked in-frame to the immunoglobulin Fc fragment.

Herein, the physiologically active polypeptide, the immunoglobulin Fc fragment, the non-peptidyl linker and the conjugate are as described above.

In still another aspect, the present invention provides a method for preparing the long-acting pharmaceutical composition, the method comprising: (a) linking a physiologically active polypeptide to an immunoglobulin Fc fragment to prepare a mixture of physiologically active polypeptide-immunoglobulin Fc fragment conjugates; and (b) separating from the mixture a physiologically active polypeptide monomer-immunoglobulin Fc fragment conjugate comprising one molecule of the physiologically active polypeptide linked to a single immunoglobulin Fc fragment.

Herein, the physiologically active polypeptide, the immunoglobulin Fc fragment, the non-peptidyl linker and the long-acting pharmaceutical composition are as described above.

Step (a) in the method of the present invention is a step of covalently linking a physiologically active polypeptide via a non-peptidyl linker to an immunoglobulin Fc fragment. Step (a) may comprise the steps of: (i) linking any one of the physiologically active polypeptide and the immunoglobulin Fc fragment to a reactive group at one end of the non-peptidyl linker; and (ii) linking the remaining one to a reactive group at the other end of the non-peptidyl linker. Step (a) may further comprise, between steps (i) and (ii), a step of separating the physiologically active polypeptide or immunoglobulin Fc fragment linked to one end of the non-peptidyl linker. For preparation of this conjugate, the disclosure of Korean Patent No. 10-0725315 may be incorporated herein by reference.

When the conjugate is prepared by this process, conjugates comprising the physiologically active polypeptide in a dimeric or multimeric form can be generated as byproducts in addition to a conjugate comprising a physiologically active monomer linked to the immunoglobulin Fc fragment.

Thus, the method of the present invention may further comprise, after step (a) of preparing the mixture of conjugates, step (b) of separating from the mixture a physiologically active polypeptide monomer-immunoglobulin Fc fragment conjugate comprising a physiologically active polypeptide monomer linked to the immunoglobulin Fc fragment.

Separation conditions in step (b) may vary depending on the kinds of non-peptidyl linker, physiologically active polypeptide and the like used.

Hereinafter, the present invention will be described in further detail with reference to examples. It is to be understood, however, that these examples are for illustrative purposes only and are not intended to limit the scope of the present invention.

EXAMPLE

Preparation of GLP-1 Agonist-immunoglobulin Fc Fragment Conjugate

A 3.4-kDa propion-ALD2 PEG (IDB, Korea) was reacted site-specifically with the lysine residue of a GLP-1 agonist. To obtain a conjugate in which PEG and the GLP-1 agonist are linked to each other at a ratio of 1:1, the reaction mixture was then subjected to cation-exchange column chromatography to purify a mono-PEGylated GLP-1 agonist. To prepare a GLP-1 agonist-immunoglobulin Fc fragment conjugate comprising the mono-PEGylated GLP-1 linked specifically to the N-terminus of the immunoglobulin Fc fragment, a reaction was performed at a pH of 5.0-8.2. After the coupling reaction, a two-step purification process was performed using a hydrophobic column and an anion-exchange column, thereby obtaining a GLP-1 agonist-immunoglobulin Fc fragment conjugate comprising the GLP-1 agonist linked site-specifically to the immunoglobulin Fc fragment.

The GLP-1 agonist-immunoglobulin Fc fragment conjugate prepared by this process was analyzed, and as a result, it was found that only a GLP-1 agonist monomer-immunoglobulin Fc fragment conjugate was present in the prepared conjugate, or a multimeric conjugate including a trace amount of a GLP-1 agonist dimer-immunoglobulin Fc fragment conjugate was present in an amount of 5% (w/w) or less based on the total weight of the prepared conjugate.

Comparative Example

Preparation of GLP-1 Agonist Dimer-immunoglobulin Fc Fragment Conjugate

A DNA sequence comprising a GLP-1 agonist linked to an immunoglobulin Fc fragment was cloned into an animal cell expression vector. The DNA encoding the recombinant protein was transfected into the animal cell line 293-F (Freestyle 293-F cell, Invitrogen) using a transfection solution (FreeStyle™ MAX Reagent, Invitrogen), and then the cells were cultured for 48 hours and the culture was harvested. The expressed GLP-1 agonist dimer-immunoglobulin Fc fragment conjugate was purified from the culture using an affinity column.

Experimental Example 1

Assessment of Receptor Internalization

PathHunter® eXpress Activated GPCR Internalization Assay was used to assess receptor internalization. Specifically, U2OS cells that express human GLP-1 receptor were seeded into a white 96-well plate and cultured for 24-48 hours. The GLP-1 agonist-immunoglobulin Fc fragment conjugate of the Example was 4-fold serially diluted from 3 µM, and the in-frame GLP-1 agonist-immunoglobulin Fc fragment conjugate of the Comparative Example was 4-fold serially diluted from 15 µM, and each of the dilutions was added to the well plate. Next, receptor internalization of each of the conjugates was induced in a $CO_2$ incubator at 37° C. for 3 hours. Then, a substrate for detecting endocytosed receptor was added to the well plate and allowed to react at room temperature for 60 minutes, and the luminescence of the plate was measured with a luminescence plate reader. The results of the measurement are shown in FIG. 2.

As a result, as shown in FIG. 2, the conjugate of the Example showed an $EC_{50}$ of 377 nM, and the conjugate of the Comparative Example showed an $EC_{50}$ of 14.59 nM, indicating that the GLP-1 agonist-immunoglobulin Fc fragment conjugate of the present invention showed significantly reduced receptor internalization compared to the GLP-1 agonist-immunoglobulin Fc fragment conjugate of the Comparative Example. Such results suggest that a conjugate comprising a physiologically active polypeptide monomer linked to an immunoglobulin Fc fragment can show reduced receptor-mediated internalization and clearance compared to a conjugate in which the physiologically active polypeptide is present in a dimeric form.

Experimental Example 2

Test for Comparison of In Vivo Pharmacokinetics Between GLP-1 Agonist-immunoglobulin Fragment Conjugates In order to compare in vivo pharmacokinetics between the GLP-1 agonist-immunoglobulin Fc fragment conjugate of the Example and the GLP-1 agonist-immunoglobulin Fc fragment conjugate, changes in the serum concentrations of the conjugates were analyzed using normal SD rats.

Specifically, each of the GLP-1 agonist-immunoglobulin Fc fragment conjugate (400 mcg/kg) and the GLP-1 agonist-immunoglobulin Fc fragment conjugate (400 mcg/kg) was diluted in physiological saline and administered subcutaneously to the animals at a dose of 2 mL/kg. At 4, 8, 24, 48, 72, 96, 120, 144, 168, 192, 216, 240, 288, 312 and 336 hours after administration of the test materials, blood was collected from the jugular vein of the rats, and serum was separated from the blood. Next, the concentration of the drug in each of the serum samples was quantified by an enzyme-linked immunosorbent assay, and the results of the quantification are shown in FIG. 3.

As a result, the serum half-lives of the GLP-1 agonist-immunoglobulin Fc fragment conjugate of the Example and the GLP-1 agonist-immunoglobulin Fc fragment conjugate of the Comparative Example were 40.9 hours and 28 hours, respectively, and the maximum serum concentrations of the conjugates were 1758.6 ng/mL and 742.7 ng/mL, respectively. In other words, when the drugs were administered subcutaneously to the normal rats at the same dose, it was shown that the monomeric GLP-1 agonist-immunoglobulin Fc fragment conjugate of the present invention was excellent in terms of the in vivo absorption and half-life compared to the dimeric GLP-1 agonist-immunoglobulin Fc fragment conjugate (FIG. 3).

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

SEQUENCE LISTING

```
<160> NUMBER OF SEQ ID NOS: 2

<210> SEQ ID NO 1
<211> LENGTH: 38
<212> TYPE: PRT
<213> ORGANISM: Artificial Sequence
<220> FEATURE:
<223> OTHER INFORMATION: GLP-1 Agonist

<400> SEQUENCE: 1

Gly Glu Gly Thr Phe Thr Ser Asp Leu Ser Lys Gln Met Glu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35
```

```
<210> SEQ ID NO 2
<211> LENGTH: 29
<212> TYPE: PRT
<213> ORGANISM: Artificial Sequence
<220> FEATURE:
<223> OTHER INFORMATION: GLP-1 Agonist

<400> SEQUENCE: 2

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly
            20                  25
```

What is claimed is:

1. A long-acting pharmaceutical composition, comprising a conjugate comprising a physiologically active polypeptide linked to an immunoglobulin Fc fragment,
    wherein the composition comprises a monomeric conjugate comprising one molecule of the physiologically active polypeptide linked to one immunoglobulin Fc chain of a single immunoglobulin Fc fragment having two immunoglobulin Fc chains, and a multimeric conjugate comprising two or more molecules of the same physiologically active polypeptide linked to a single immunoglobulin Fc fragment having two immunoglobulin Fc chains, provided that the molar ratio of the monomeric conjugate to the multimeric conjugate in the composition is at least 19;
    wherein each of the two immunoglobulin Fc chains in the multimeric conjugate is linked to one or more molecules of the physiologically active polypeptide;
    wherein the monomeric conjugate shows reduced receptor-mediated internalization or receptor-mediated clearance compared to either a dimeric conjugate comprising two molecules of the physiologically active polypeptide linked via a non-peptidyl linker to a single immunoglobulin Fc fragment, or a conjugate comprising a physiologically active polypeptide dimer linked in-frame to the immunoglobulin Fc fragment; and
    wherein the physiologically active polypeptide is selected from the group consisting of glucagon-like peptide-1 (GLP-1), glucagon, oxyntomodulin, insulin, growth hormone releasing hormone, growth hormone releasing peptide, interferon receptors, interleukins, interleukin receptors, macrophage activating factor, macrophage peptide, B cell factor, T cell factor, protein A, cell necrosis glycoproteins, lymphotoxin, tumor necrosis factor, alpha-1 antitrypsin, albumin, α-lactalbumin, apolipoprotein-E, angiopoietins, hemoglobin, thrombin, thrombin receptor activating peptide, thrombomodulin, blood factors VII, VIIa, VIII, IX and XIII, plasminogen activating factor, urokinase, streptokinase, hirudin, protein C, C-reactive protein, superoxide dismutase, leptin, platelet-derived growth factor, epithelial growth factor, epidermal growth factor, angiostatin, angiotensin, alcitonin, atriopeptin, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, cholecystokinin, pancreatic polypeptide, gastrin releasing peptide, corticotropin releasing factor, thyroid stimulating hormone, autotaxin, lactoferrin, and myostatin.

2. The long-acting pharmaceutical composition of claim 1, wherein the conjugate further comprises a non-peptidyl linker interposed between the physiologically active polypeptide and the immunoglobulin Fc frgagment to link the physiological active polypeptide to the immunoglobulin Fc fragment.

3. The long-acting pharmaceutical composition of claim 2, wherein the non-peptidyl linker is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and combinations thereof.

4. The long-acting pharmaceutical composition of claim 2, wherein the non-peptidyl linker has a molecular weight ranging from 1 to 100 kDa.

5. The long-acting pharmaceutical composition of claim 1, wherein the physiologically active polypeptide is selected from the group consisting of glucagon-like peptide-1 (GLP-1), glucagon, oxyntomodulin, insulin, and derivatives thereof.

6. The long-acting pharmaceutical composition of claim 1, wherein the immunoglobulin Fc fragment is composed of 1 to 4 domains selected from the group consisting of CH1, CH2, CH3 and CH4 domains.

7. The long-acting pharmaceutical composition of claim 1, wherein the immunoglobulin Fc fragment further comprises a hinge region.

8. The long-acting pharmaceutical composition of claim 1, wherein the immunoglobulin Fc fragment is an Fc fragment derived from one selected from the group consisting of IgG, IgA, IgD, IgE, IgM, combinations thereof and hybrids thereof.

9. The long-acting pharmaceutical composition of claim 1, wherein the immunoglobulin Fc fragment is an IgG4 Fc fragment.

10. The long-acting pharmaceutical composition of claim 1, wherein the immunoglobulin Fc fragment is non-glycosylated.

11. A method for preparing the long-acting pharmaceutical composition of claim 1, comprising:
    (a) linking a physiologically active polypeptide to an immunoglobulin Fc fragment having two immunoglobulin Fc chains to prepare a mixture of physiologically active polypeptide-immunoglobulin Fc fragment conjugates; and (b) separating from the mixture a physiologically active polypeptide monomer-immunoglobulin Fc fragment conjugate comprising one molecule of the physiologically active polypeptide linked to one immunoglobulin Fc chain of a single immunoglobulin Fc fragment having two immunoglobulin Fc chains.

12. The method of claim 11, wherein the physiologically active polypeptide and the immunoglobulin Fc fragment are linked to each other via a non-peptidyl linker.

13. The method of claim 11, wherein the conjugate of the long-acting pharmaceutical composition, which comprises one molecule of the physiologically active polypeptide linked to one immunoglobulin Fc chain of a single immunoglobulin Fc fragment having two immunoglobulin Fc chains, shows reduced receptor-mediated internalization or receptor-mediated clearance compared to either a dimeric conjugate comprising two molecules of the physiologically active polypeptide linked via the non-peptidyl linker to a single immunoglobulin Fc fragment having two immunoglobulin Fc chains, or a physiologically active polypeptide dimer linked in-frame to the immunoglobulin Fc fragment.

* * * * *

UNITED STATES PATENT AND TRADEMARK OFFICE
CERTIFICATE OF CORRECTION

Page 1 of 2

PATENT NO.        : 10,487,128 B2
APPLICATION NO.   : 14/904254
DATED             : November 26, 2019
INVENTOR(S)       : Sung Hee Park et al.

It is certified that error appears in the above-identified patent and that said Letters Patent is hereby corrected as shown below:

In the Specification

<u>Sequence Listing</u>
Columns 15 and 16, Line 47, delete:

"
```
<210> SEQ ID NO 1
<211> LENGTH: 38
<212> TYPE: PRT
<213> ORGANISM: Artificial Sequence
<220> FEATURE:
<223> OTHER INFORMATION: GLP-1 Agonist

<400> SEQUENCE: 1

Gly Glu Gly Thr Phe Thr Ser Asp Leu Ser Lys Gln Met Glu Glu Glu
1               5                   10                  15

Ala Val Arg Leu Phe Ile Glu Trp Leu Lys Asn Gly Gly Pro Ser Ser
                20                  25                  30

Gly Ala Pro Pro Pro Ser
            35
```
"

Signed and Sealed this
Seventh Day of July, 2020

Andrei Iancu
*Director of the United States Patent and Trademark Office*

CERTIFICATE OF CORRECTION (continued)
U.S. Pat. No. 10,487,128 B2

And insert:

```
<210> SEQ ID NO 1
<211> LENGTH: 38
<212> TYPE:   PRT
<213> ORGANISM:  Artificial Sequence
<220> FEATURE:
<223> OTHER INFORMATION:  GLP-1 Agonist
<220> FEATURE:
<221> OTHER INFORMATION: MISC_FEATURE
<222> LOCATION:  (1)
<223> OTHER INFORMATION:  1H-imidazol-4-yl-acetyl is linked to the
      amino group of Gly <400>    1
Gly Glu Gly Thr Phe Thr Ser Asp Leu Ser Lys Gln Met Glu Glu Glu
  1               5                  10                  15

Ala Val Arg Leu Phe Ile Glu Trp Leu Lys Asn Gly Gly Pro Ser Ser
                 20                  25                  30

Gly Ala Pro Pro Pro Ser
                 35
```

-- therefor.